(12) United States Patent
Tanaka et al.

(10) Patent No.: US 11,521,765 B2
(45) Date of Patent: Dec. 6, 2022

(54) TUBE EQUIPPED ELECTRIC WIRE

(71) Applicant: Hitachi Metals, Ltd, Tokyo (JP)

(72) Inventors: Kotaro Tanaka, Tokyo (JP); Takanobu Watanabe, Tokyo (JP); Kimika Kudo, Tokyo (JP); Takanori Komuro, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 17/216,006

(22) Filed: Mar. 29, 2021

(65) Prior Publication Data

US 2021/0304919 A1 Sep. 30, 2021

(30) Foreign Application Priority Data

Mar. 31, 2020 (JP) .............................. JP2020-062249

(51) Int. Cl.
*H01B 7/04* (2006.01)
*A61M 25/00* (2006.01)

(52) U.S. Cl.
CPC .............. *H01B 7/04* (2013.01); *A61M 25/00* (2013.01)

(58) Field of Classification Search
CPC ........................................................ H01P 1/16
USPC ......................................................... 138/22
See application file for complete search history.

(56) References Cited

U.S. PATENT DOCUMENTS

| | | | | |
|---|---|---|---|---|
| 1,481,078 A | * | 1/1924 | Albertson | F16C 1/06 464/57 |
| 2,211,975 A | * | 8/1940 | Hendrickson | A61M 25/005 138/133 |
| 2,409,304 A | * | 10/1946 | Morrison | F16L 53/70 138/28 |
| 3,568,660 A | * | 3/1971 | Crites | A61N 1/056 29/850 |
| 3,750,058 A | * | 7/1973 | Bankert, Jr. | H01P 1/00 333/251 |
| 4,130,904 A | * | 12/1978 | Whalen | A61F 2/06 623/1.13 |
| 4,270,690 A | * | 6/1981 | Mabery | F28F 13/12 72/283 |
| 4,325,374 A | * | 4/1982 | Komiya | A61B 18/14 606/47 |
| 4,437,467 A | * | 3/1984 | Helfer | A61B 5/02411 600/376 |
| 4,498,473 A | * | 2/1985 | Gereg | A61M 16/0418 128/207.14 |
| 4,528,810 A | * | 7/1985 | Vogelsberg | G02B 6/449 57/293 |
| 4,676,229 A | * | 6/1987 | Krasnicki | A61B 1/042 600/153 |
| 4,759,346 A | * | 7/1988 | Nakajima | A61B 1/05 600/113 |

(Continued)

FOREIGN PATENT DOCUMENTS

JP H08-155031 A 6/1996

*Primary Examiner* — Krystal Robinson
(74) *Attorney, Agent, or Firm* — McGinn I.P. Law Group, PLLC.

(57) ABSTRACT

A tube equipped electric wire, which is configured to be used in a catheter equipped with a catheter tube and be installed within the catheter tube, is composed of a tube including an outer surface, and one or more electric wires helically wound around the outer surface of the tube.

20 Claims, 2 Drawing Sheets

(56) References Cited

U.S. PATENT DOCUMENTS

| | | | | |
|---|---|---|---|---|
| 4,900,303 | A | * | 2/1990 | Lemelson ......... A61M 37/0069 |
| | | | | 604/11 |
| 4,982,765 | A | * | 1/1991 | Usui ..................... F16L 11/112 |
| | | | | 138/133 |
| 5,057,092 | A | * | 10/1991 | Webster, Jr. ........ A61M 25/005 |
| | | | | 138/123 |
| 5,231,681 | A | * | 7/1993 | Bergqvist ................. G01K 5/46 |
| | | | | 374/E5.028 |
| 5,366,493 | A | * | 11/1994 | Scheiner .................. A61N 1/05 |
| | | | | 607/116 |
| 5,630,806 | A | * | 5/1997 | Inagaki ............. A61M 25/0045 |
| | | | | 604/524 |
| 5,702,373 | A | * | 12/1997 | Samson .............. A61M 25/005 |
| | | | | 604/526 |
| 6,217,566 | B1 | * | 4/2001 | Ju ..................... A61M 25/0052 |
| | | | | 604/526 |
| 8,639,352 | B2 | * | 1/2014 | Wang ................... A61N 1/0472 |
| | | | | 607/116 |
| 9,925,354 | B2 | * | 3/2018 | Scott .................... A61B 5/6852 |
| 10,188,421 | B2 | * | 1/2019 | Spiel .................. A61B 17/3401 |
| 2001/0029061 | A1 | * | 10/2001 | Carlson .................... H01L 24/83 |
| | | | | 257/E21.508 |
| 2008/0073099 | A1 | * | 3/2008 | Howard .................... F02C 7/00 |
| | | | | 174/28 |
| 2011/0087257 | A1 | * | 4/2011 | To .................. A61B 17/320758 |
| | | | | 606/170 |
| 2014/0236125 | A1 | * | 8/2014 | Watanabe ....... A61M 25/09033 |
| | | | | 604/528 |

* cited by examiner

TUBE EQUIPPED ELECTRIC WIRE

CROSS-REFERENCE TO RELATED APPLICATION

The present application is based on Japanese patent application No. 2020-062249 filed on Mar. 31, 2020, the entire contents of which are incorporated herein by reference.

BACKGROUND OF THE INVENTION

1. Field of the Invention

The present invention relates to a tube equipped electric wire.

2. Description of the Related Art

Conventionally, there is known a catheter with a tube (inner tube) for a drug or the like to be passed therethrough and one or more electric wires being installed within a catheter tube (outer tube). The one or more electric wires are configured to be connected to a medical diagnosis or treatment component provided on a tip portion of the catheter, such as a sensor or an electrode or the like.

Note that there is JPH8-155031A as prior art document information related to the invention of this application.

[Patent Document 1] JPH8-155031A

SUMMARY OF THE INVENTION

In the aforementioned catheter, fine and flexible electric wires have been used in order for the catheter to be kept flexible and in order to be installed in the catheter tube designed fine. For that reason, there has been a problem with it being very time consuming to insert the one or more electric wires and the inner tube into the catheter tube.

In light of the foregoing, it is an object of the present invention to provide a tube equipped electric wire, which is configured to be able to facilitate the insertion together of one or more electric wires and a tube into a catheter tube, so that a catheter is easy to produce.

For the purpose of solving the above problem, the present invention provides a tube equipped electric wire, which is configured to be used in a catheter equipped with a catheter tube and be installed within the catheter tube, comprising a tube; and one or more electric wires helically wound around an outer surface of the tube.

Points of the Invention

According to the present invention, it is possible to provide the tube equipped electric wire, which is configured to be able to facilitate the insertion together of the one or more electric wires and the tube into the catheter tube, so that the catheter is easy to produce.

DETAILED DESCRIPTION OF THE PREFERRED EMBODIMENTS

Embodiment

An embodiment of the present invention will be described below in conjunction with the accompanying drawings.

Figure 1A:
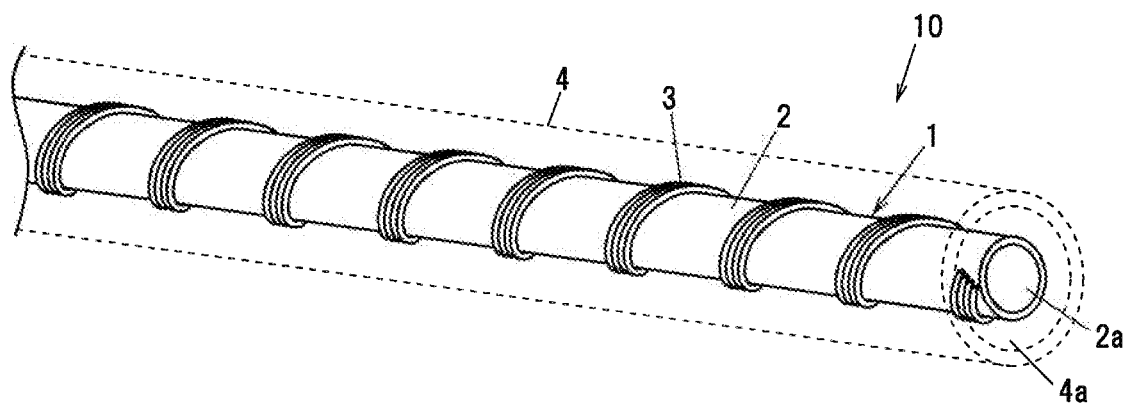
FIG. 1A is a perspective view showing a tube equipped electric wire according to one embodiment of the present invention.
Figure 1B:
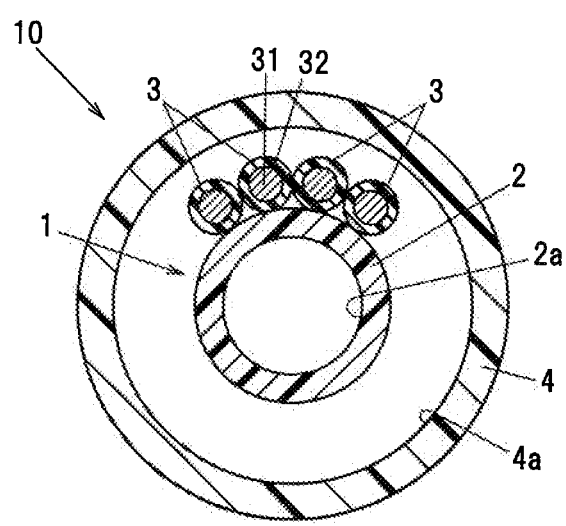
FIG. 1B is a cross-sectional view showing a cross section perpendicular to a longitudinal direction of the inner tube 2 equipped electric wire shown in FIG. 1A.

FIG. 1A is a perspective view showing a tube equipped electric wire according to the present embodiment, and FIG. 1B is a cross-sectional view showing a cross section perpendicular to a longitudinal direction of the inner tube 2 equipped electric wire shown in FIG. 1A.

As shown in FIGS. 1A and 1B, the tube equipped electric wire 1 is configured in such a manner as to include a tube (inner tube) 2, and one or more electric wires 3. A catheter 10 is configured with the tube equipped electric wire 1 being installed within a catheter tube (outer tube) 4.

The inner tube 2 includes, for example, a hollow portion 2a for a drug or the like to be passed therethrough. The inner tube 2 is formed in a circular cylindrical shape, and the hollow portion 2a of the inner tube 2 is formed in a central portion of the inner tube 2 (a central portion in the cross-section perpendicular to the longitudinal direction of the inner tube 2) in such a manner as to extend along the longitudinal direction of the inner tube 2. The inner tube 2 may be configured in such a manner as to be made of a material harder than that for the catheter tube 4, in order to be easily inserted into the catheter tube 4. In the present embodiment, the inner tube 2 made of a PEEK (polyether ether ketone) is used. The outer diameter of the inner tube 2 is, e.g., 0.6 mm to 2.0 mm, and the thickness of the inner tube 2 is e.g., 0.06 mm to 0.3 mm. In the present embodiment the outer diameter of the inner tube 2 is 1.0 mm and the thickness of the inner tube 2 is 0.1 mm (Namely, the inner diameter of the inner tube 2 is 0.8 mm).

The catheter tube 4 is the one designed for the inner tube 2 and the one or more electric wires 3 to be installed therein, and includes a hollow portion 4a for the above inner tube 2 and the above one or more electric wires 3 to be installed therein. The catheter tube 4 is formed in a circular cylindrical shape, and the hollow portion 4a of the catheter tube 4 is formed in a central portion of the catheter tube 4 (a central portion in the cross-section perpendicular to the longitudinal direction of the catheter tube 4) in such a manner as to extend along the longitudinal direction of the catheter tube 4. The catheter tube 4 is configured in such a manner as to be made of a flexible material such as a polyethylene or the like. The outer diameter of the catheter tube 4 is, e.g., 0.8 mm to 2.5 mm, and the thickness of the catheter tube 4 is e.g., 0.06 mm to 0.5 mm. In the present embodiment the outer diameter of the catheter tube 4 is 1.8 mm and the thickness of the catheter tube 4 is 0.1 mm (Namely, the inner diameter of the inner tube 2 is 1.6 mm) 1.8 mm, and the inner diameter of the catheter tube 4 is, e.g., 1.6 mm.

The one or more electric wires 3 are configured to be connected to a medical diagnosis or treatment component provided on a tip portion of the catheter 10, such as a sensor or an electrode or the like, and to be used in applications for signal transmission or power supply. The one or more electric wires 3 are each configured to include a conductor 31, and an electrical insulating member 32 made of an electrical insulative resin that is provided over that respective conductor 31. In order to ensure the flexibility of the one or more electric wires 3, a stranded wire conductor composed of a plurality of constituent metal wires each made of a copper or the like being stranded together may be used as each of the conductors 31 of the one or more electric wires 3. Herein, a case where four of the electric wires 3 are used will be described, but the number of electric wires 3 may be not smaller than one and not larger than three, or five or more. For the one or more electric wires 3, the electric wires 3 configured relatively fine are used in order that they can be inserted into the catheter tube 4 designed fine. The outer diameters of the one or more electric wires 3 are, e.g., 0.06 mm to 0.30 mm. In the present embodiment, the outer diameters of the one or more electric wires 3 are 0.2 mm.

In the present embodiment, the one or more electric wires 3 are wound helically and directly around the outer surface of the inner tube 2. The one or more electric wires 3 are so-called curl cords having a shape memory property that allows them to revert to their helical shape, and the one or more electric wires 3 are maintained in a state of being wound around the periphery of the inner tube 2 by being subjected to a permanent bending. Further, the four electric wires 3 are wound helically around the outer surface of the inner tube 2 in a state of being aligned in the circumferential direction of the inner tube 2.

Employing the aforementioned configuration of the catheter 10 enables the one or more electric wires 3 configured to be fine and flexible, together with the inner tube 2, to be easily inserted into the catheter tube 4 and, as a result, it is possible to easily insert the one or more electric wires 3 and the inner tube 2 together into the catheter tube 4. Further, by the one or more electric wires 3 being wound helically around the outer surface of the inner tube 2, the catheter 10 is suppressed from becoming resistant to being bent to a particular direction and, as a result, the catheter 10 is easy to bend in all directions. When the thickness of the inner tube 2 is too thin, the strength and the stiffness of the inner tube 2 would not be sufficient, so that the inner tube 2 may easily kink (i.e., bend, collapse) due to the one or more electric wires 3 being helically wound. Therefore, the thickness of the inner tube 2 is preferably not less than 0.06 mm.

In the present embodiment, the one or more electric wires 3 are not being fixed to the inner tube 2 by adhesion or the like, but are provided on the outer surface of the inner tube 2 in such a manner as to be movable in the longitudinal direction of the inner tube 2. This, in the termination working of the tube equipped electric wire 1, enables the inner tube 2 and the one or more electric wires 3 to be easily separated from each other, and the one or more electric wires 3 to be easily pulled out from the catheter tube 4 and, as a result, the termination workability of the tube equipped electric wire 1 is enhanced.

The helical winding pitches of the one or more electric wires 3 may be set at not shorter than 1.8 times and not longer than 30 times the outer diameter of the inner tube 2. By the helical winding pitches of the one or more electric wires 3 being set to be no longer than 30 times the outer diameter of the inner tube 2, the one or more electric wires 3 become resistant to slipping off the inner tube 2. In addition, by the helical winding pitches of the one or more electric wires 3 being set at not shorter than 1.8 times the outer diameter of the inner tube 2, the one or more electric wires 3 can be suppressed from being wastefully lengthened, and besides, the time taken for the step of helically winding the one or more electric wires 3 also cannot become longer than necessary and, as a result, it is possible to ensure a reduction in cost.

In the present embodiment, since the one or more electric wires 3 are helically wound around the outer surface of the inner tube 2, in the tube equipped electric wire 1 having a predetermined length, the lengths of the one or more electric wires 3 included in that tube equipped electric wire 1 are longer than the length of the inner tube 2. As a result of the one or more electric wires 3 being long, the one or more electric wires 3 become high in their apparent resistance. The lengths of the one or more electric wires 3 can be adjusted according to the helical winding pitches of the one or more electric wires 3. The lengths of the one or more electric wires 3 may be set to be not longer than 2.0 times the length of the inner tube 2, in order to suppress the one or more electric wires 3 from slipping off the inner tube 2, and in order to suppress the one or more electric wires 3 from becoming high in their apparent resistance.

(Producing Method for the Catheter 10)

First, the tube equipped electric wire 1 is produced. In the production of the tube equipped electric wire 1, first, each of the inner tube 2, the one or more electric wires 3, and the catheter tube 4 is formed. In the formation of the inner tube 2, a circular columnar core member is formed preliminarily by extrusion molding or the like, and the inner tube 2 is extruded and molded on that core member by tube extrusion. After that, the one or more electric wires 3 are helically wound around the outer surface of the inner tube 2, which may be followed by removal of the same core member. Also, in the formation of the catheter tube 4, in the same manner, a circular columnar core member is formed preliminarily by extrusion molding or the like, and the catheter tube 4 is extruded and molded on that core member by tube extrusion, which may be followed by removal of the same core member.

After that, the inner tube 2 around which the one or more electric wires 3 have been wound, in other words, the tube equipped electric wire 1 is inserted into the catheter tube 4. In the present embodiment, since the fine and flexible one or more electric wires 3 are inserted into the catheter tube 4 along with the inner tube 2, the insertion together of the one or more electric wires 3 and the inner tube 2 into the catheter tube 4 is facilitated. Note that it is possible to make the flexibility of the catheter 10 high by providing the tube equipped electric wire 1 in such a manner as to be movable between it and the catheter tube 4.

(Modification)

Figure 2:
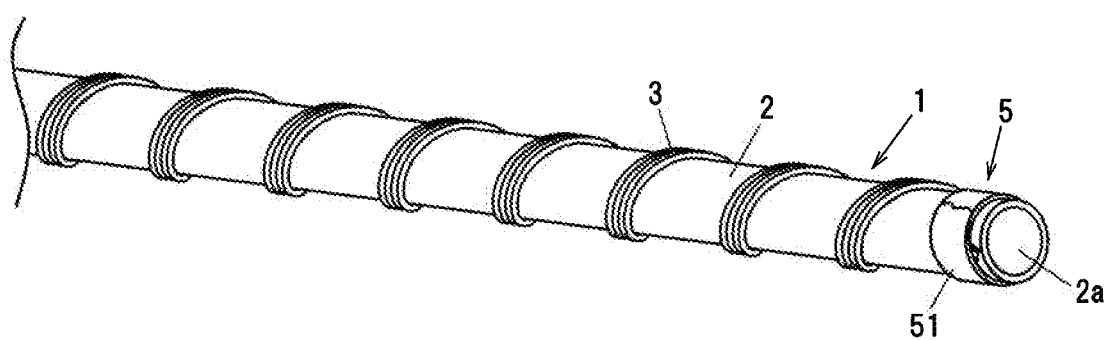
FIG. 2 is a perspective view of a tube equipped electric wire according to one modification to the present invention.

In the present embodiment, the tube equipped electric wire 1 is configured in such a manner that the one or more electric wires 3 being helically wound around the outer surface of the inner tube 2 are not being fixed to the same inner tube 2, but the tube equipped electric wire 1 may be configured in such a manner that the one or more electric wires 3 being helically wound around the outer surface of the inner tube 2 are partially being fixed to the same inner tube 2. For example, as shown in FIG. 2, the tube equipped electric wire 1 may be configured to have, at an end part of the inner tube 2, a fixing portion 5, which is configured to fix the one or more electric wires 3 to the same inner tube 2. By the one or more electric wires 3 being fixed to the inner tube 2 at the end part of the same inner tube 2, when the inner tube 2 and the one or more electric wires 3 are inserted together into the catheter tube 4, the one or more electric wires 3 are suppressed from being slid on the outer surface of the inner tube 2 (the one or more electric wires 3 are suppressed from being moved in the longitudinal direction of the inner tube 2) and, as a result, the insertion together of the one or more electric wires 3 and the inner tube 2 into the catheter tube 4 is further facilitated. Further, the fixing portion 5 also acts to suppress the one or more electric wires 3 and the inner tube 2 from being pulled apart before the termination working of the tube equipped electric wire 1, and thereby enhance the handleability of the tube equipped electric wire 1.

In the example of the tube equipped electric wire 1 shown in FIG. 2, the fixing portion 5 is formed by winding an adhesive tape 51 around the peripheries of the inner tube 2 and the one or more electric wires 3 together at the end part of the same inner tube 2. The adhesive tape 51 can easily be removed at the time of the termination working of the tube equipped electric wire 1, and is suitable for use as the fixing portion 5. It should be noted, however, that the fixing portion 5 is not limited to the above adhesive tape 51, but that the fixing portion 5 can be configured by adhesively fixing the end portions of the one or more electric wires 3 to the outer surface of the inner tube 2 at the end part of the same inner tube 2 with an adhesive, for example.

(Actions and Advantageous Effects of the Embodiment)

As described above, the tube equipped electric wire 1 according to the present embodiment is configured in such a manner as to include the inner tube 2, and the one or more electric wires 3 helically wound around the outer surface of the inner tube 2.

By helically winding the one or more electric wires 3 around the inner tube 2, even when using the one or more electric wires 3 configured fine and flexible, it is possible to easily insert the one or more electric wires 3 along with the inner tube 2 into the catheter tube 4 and, as a result, the production of the catheter 10 is facilitated. Also, by the one or more electric wires 3 being wound helically around the inner tube 2, the catheter 10 is easy to bend in all directions.

SUMMARY OF THE EMBODIMENT

Next, the technical ideas grasped from the aforementioned embodiments will be described with the aid of the reference characters and the like in the embodiments. It should be noted, however, that each of the reference characters and the like in the following descriptions is not to be construed as limiting the constituent elements in the appended claims to the members and the like specifically shown in the embodiments.

[1] A tube equipped electric wire (1), which is configured to be used in a catheter (10) equipped with a catheter tube (4) and be installed within the catheter tube (4), comprising: a tube (2); and one or more electric wires (3) helically wound around an outer surface of the tube (2).

[2] The tube equipped electric wire (1) as defined in the above [1], wherein helical winding pitches of the one or more electric wires (3) are not shorter than 1.8 times and not longer than 30 times an outer diameter of the tube (2).

[3] The tube equipped electric wire (1) as defined in the above [1] or [2], wherein lengths of the one or more electric wires (3) are not longer than 2.0 times a length of the tube (2).

[4] The tube equipped electric wire (1) as defined in any one of the above [1] to [3], wherein the one or more electric wires (3) are provided on the outer surface of the tube (2) in such a manner as to be movable in a longitudinal direction of the tube (2).

[5] The tube equipped electric wire (1) as defined in the above [4], further comprising, at an end part of the tube (2), a fixing portion (5) configured in such a manner as to fix the one or more electric wires (3) to the tube (2).

[6] The tube equipped electric wire (1) as defined in the above [5], wherein the fixing portion (5) comprises an adhesive tape (51) wound around the tube (2) and the one or more electric wires (3) at the end part of the tube (2).

Although the embodiments of the present invention have been described above, the aforementioned embodiments are not to be construed as limiting the inventions according to the appended claims. Further, it should be noted that not all the combinations of the features described in the embodiments are indispensable to the means for solving the problem of the invention.

Further, the present invention can appropriately be modified and implemented without departing from the spirit of the present invention. For example, in the above embodiments, the tube equipped electric wire 1 is configured in such a manner that the one or more electric wires 3 and the inner tube 2 are separable from each other except for being fixed to each other at the location of the fixing portion 5, but the tube equipped electric wire 1 may be configured in such a manner that the one or more electric wires 3 are fixed to the inner tube 2, as long as the one or more electric wires 3 can easily be pulled off by pulling the one or more electric wires 3. For example, the one or more electric wires 3 may be fixed to the inner tube 2 by melting the surfaces of the electrical insulating members 32 of the one or more electric wires 3, or a part of the outer surface of the inner tube 2 by heat.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A tube equipped electric wire comprising: a tube; and one or more electric wires helically wound around an outer surface of the tube,
   wherein the tube equipped electric wire is configured to be:
   used in a catheter equipped with a catheter tube; and installed within the catheter tube, and
   wherein the tube is composed of a material harder than a material of the catheter tube.

2. The tube equipped electric wire according to claim 1, wherein helical winding pitches of the one or more electric wires are not shorter than 1.8 times and not longer than 30 times an outer diameter of the tube.

3. The tube equipped electric wire according to claim 2, wherein lengths of the one or more electric wires are adjusted by changing the helical winding pitches.

4. The tube equipped electric wire according to claim 3, wherein the lengths of the one or more electric wires are less than 2 times a length of the tube.

5. The tube equipped electric wire according to claim 1, wherein lengths of the one or more electric wires are not longer than 2.0 times a length of the tube.

6. The tube equipped electric wire according to claim 1, wherein the one or more electric wires are provided on the outer surface of the tube in such a manner as to be movable in a longitudinal direction of the tube.

7. The tube equipped electric wire according to claim 6, further comprising:
   at an end part of the tube, a fixing portion configured in such a manner as to fix the one or more electric wires to the tube.

8. The tube equipped electric wire according to claim 7, wherein the fixing portion comprises an adhesive tape wound around the tube and the one or more electric wires.

9. The tube equipped electric wire according to claim 1, wherein the tube comprises polyether ether ketone, and wherein the tube has an outer diameter of 0.6 mm to 2.0 mm and a thickness of 0.06 mm to 0.3 mm.

10. The tube equipped electric wire according to claim 1, wherein the tube comprises polyether ether ketone.

11. The tube equipped electric wire according to claim 1, wherein the tube has an outer diameter of 0.6 mm to 2.0 mm and a thickness of 0.06 mm to 0.3 mm.

12. The tube equipped electric wire according to claim 11, wherein the tube has an outer diameter of 1.0 mm and a thickness of 0.1 mm.

13. The tube equipped electric wire according to claim 1, wherein an inner diameter of the catheter tube is greater than an outer diameter of the tube.

14. The tube equipped electric wire according to claim 1, wherein the tube includes a flat outer surface,
    wherein the one or more electric wires are provided on the outer surface of the tube in such a manner as to be movable in a longitudinal direction of the tube, and
    wherein winding pitches of the one or more electric wires are adjustable.

15. The tube equipped electric wire according to claim 1, wherein the tube is a single tube having a flat outer surface,
    wherein the one or more electric wires are helically wound directly on the outer surface of the tube,
    wherein the one or more electric wires are provided on the outer surface of the tube in such a manner as to be movable in a longitudinal direction of the tube, and
    wherein winding pitches of the one or more electric wires are adjustable.

16. The tube equipped electric wire according to claim 1, further comprising a fixing portion, only at an end part of the tube, configured in such a manner as to fix the one or more electric wires to the tube.

17. The tube equipped electric wire according to claim 1, wherein the one or more electric wires are provided on the outer surface of the tube in such a manner as to be movable in a longitudinal direction of the tube,
    wherein lengths of the one or more electric wires are adjustable by adjusting winding pitches of the one or more electric wires,
    wherein the one or more electric wires are fixed only at one end of the tube.

18. The tube equipped electric wire according to claim 1, wherein the one or more electric wires are not fixedly attached to an outer surface of the tube except at one end of the tube.

19. The tube equipped electric wire according to claim 1, wherein the one or more electric wires include a shape memory property that allows them to revert to their helical shape.

20. The tube equipped electric wire according to claim 19, wherein the one or more electric wires are maintained in a state of being wound around a periphery of the tube by being subjected to a permanent bending.

* * * * *